United States Patent [19]

Preiss et al.

[11] 4,389,489
[45] Jun. 21, 1983

[54] OPTICALLY PURE HETEROCYCLIC AMINOACID COMPOUNDS, A PROCESS FOR THEIR USE FOR THE SYNTHESIS OF MEDICAMENTS

[75] Inventors: Michael Preiss; Hermann Schutt, both of Wuppertal, Fed. Rep. of Germany

[73] Assignee: Bayer Aktiengesellschaft, Leverkusen, Fed. Rep. of Germany

[21] Appl. No.: 274,083

[22] Filed: Jun. 15, 1981

Related U.S. Application Data

[62] Division of Ser. No. 163,359, Jun. 26, 1980, abandoned.

[30] Foreign Application Priority Data

Jul. 7, 1979 [DE] Fed. Rep. of Germany ....... 2927534

[51] Int. Cl.³ ...................... C07B 19/02; C12P 13/04; 549 493
[52] U.S. Cl. .................................... 435/280; 435/106
[58] Field of Search ................................ 435/106, 280

[56] References Cited

U.S. PATENT DOCUMENTS 3,963,573 6/1976 Stauffer .......................... 435/280 X
4,202,943 5/1980 Suhara et al. ...................... 435/280
4,260,684 4/1981 Schutt ............................... 435/106

OTHER PUBLICATIONS

Morihara et al, Arch. Biochem. Biophys. 129, (1969), 620–634.
Chemical Reviews 46, 119–122, (1950).

Primary Examiner—Lionel M. Shapiro
Attorney, Agent, or Firm—Sprung, Horn, Kramer & Woods

[57] ABSTRACT

The invention relates to optically pure heterocyclic amino acid compounds of the Formula I, as described hereinabove as well as a process for their preparation involving subject D, L-compounds to the action of a proteolytic enzyme. The compounds obtained are useful, inter alia, as intermediates for the manufacture of cephalosporins or penicillins.

4 Claims, No Drawings

OPTICALLY PURE HETEROCYCLIC AMINOACID COMPOUNDS, A PROCESS FOR THEIR USE FOR THE SYNTHESIS OF MEDICAMENTS

This is a, division, of application Ser. No. 163,359, filed June 26, 1980, now abandoned.

The present invention relates to certain optically pure heterocyclic aminoacid compounds, to an enzymatic process for their production by stereoselective resolution of suitable heterocyclic D,L-aminoacid derivatives and subsequent conversion of the products into the D- and L-aminoacids, and to their use as intermediate products for the synthesis of medicaments.

According to the present invention there are provided compounds which are optically pure heterocyclic aminoacids of the formula

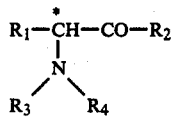

or a salt (particularly an acid-addition salt or, where a free carboxylic acid is involved, an alkali or alkaline earth salt) thereof, in which $R_1$ denotes a saturated or unsaturated, optionally substituted heterocyclic radical which contains 1 to 4 identical or different heteroatoms selected from oxygen, sulphur and nitrogen and is optionally benzo-fused, $R_2$ denotes a hydroxyl group, a $C_1$ to $C_4$ alkoxy group or a $N(R_5)_2$ radical, $R_3$ and $R_4$ independently denote a hydrogen atom, an acyl radical or a $C_2$ to $C_4$ alkenyl radical which is substituted by $C_1$ to $C_4$ alkoxycarbonyl and $R_5$ denotes a hydrogen atom or a $C_1$ to $C_4$ alkyl group, and in which the carbon atom marked with * is in either the D-form of the L-form.

Examples of preferred heterocyclic radicals of $R_1$ are pyrazolyl, imidazolyl, oxazolyl, oxdiazolyl, thiazolinyl, tetrazolyl, sydononyl, pyridyl, pyrazyl, pyrimidinyl, pyridazyl, quinolyl, isoquinolyl, quinazolyl, indolyl and indazolyl, and, particularly preferably, furyl, thienyl, pyrrolyl, thiazolyl, isothiazolyl, isoxazolyl and thiadiazolyl. The heterocyclic radicals optionally carry one or more, preferably 1 or 2, identical or, preferably, different substituents, examples of possible substituents being halogen, such as fluorine, chlorine and bromine, alkyl with 1 to 6, preferably 1 to 4 carbon atoms, amino, nitro, cyano, sulpho, $C_1$ to $C_4$ alkylsulphonyl, hydroxyl or oxo.

Acyl radicals of $R_3$ and/or $R_4$ are, preferably carboxylic acid acyl, such as optionally substituted $C_1$ to $C_6$ alkylcarbonyl or $C_1$ to $C_6$ alkoxycarbonyl, possible substitients being phenyl (which is optionally itself substituted by methyl, methoxy, chlorine, bromine, nitro or cyano), carboxyl or amino.

Particularly preferred compounds of the present invention are thus those in which $R_1$ is a heterocyclic radical selected from those preferred heterocyclic radicals mentioned above and $R_3$ and $R_4$ independently denote a hydrogen atom or a preferred acyl radical as mentioned above.

Most preferably, $R_3$ represents a hydrogen atom and $R_4$ represents a hydrogen atom or a formyl, acetyl, tert.-butoxycarbonyl, benzyloxycarbonyl or 1-methyl-2-$C_1$ to $C_4$ alkoxycarbonylvinyl radical.

According to the present invention there is further provided a process for the production of a compound of the invention in which a proteolytic enzyme bonded to a carrier is allowed to act on the racemic compounds of the formula (I) as given previously in which $R_1$, $R_3$ and $R_5$ have the meanings given in the definition of formula (I) and $R_2$ denotes a $C_1$ to $C_4$ alkoxy group or a $N(R_5)_2$ radical and $R_4$ denotes an acyl radical, or a $C_2$ to $C_4$ alkenyl radical which is substituted by $C_1$ to $C_4$ alkoxycarbonyl, in a twophase medium consisting of water and a water-immiscible solvent, the unchanged D-compound is separated off from the L-compound of the formula

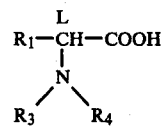

in which $R_1$, $R_3$ and $R_4$ have the abovementioned meaning, and the D- and L-compounds which have been separated from each other are, if desired, converted into compounds of the formula (I) in which $R_2$ denotes a hydroxyl group and $R_3$ and $R_4$ denote hydrogen atoms, and in the case of the L-compound, if desired, the carboxyl group is converted into a —$COR_2$ group in which $R_2$ denotes a $C_1$ to $C_4$ alkoxy group or a $N(R_5)_2$ radical in which $R_5$ has the abovementioned meaning.

The process according to the invention is thus based on converting the ester or amide group CO—$R_2$ in the L-compounds into the carboxyl group, whilst the D-compound does not undergo this hydrolysis. If the optically pure D-form is to be obtained, care should be taken that hydrolysis of the L-derivative is complete, on the other hand, if the optically pure L-form is to be obtained, hydrolysis of the L-esters and -amides should not be carried out to completion.

The optically pure compounds of the formula (I) can be used for the preparation of optically pure penicillins and cephalosporins which have hitherto been available only as epimer mixtures and are known, for example, from German Offenlegungsschriften Nos. 2,732,283 and 2,810,083. The compounds according to the invention can also be used for the preparation of penicillins and cephalosporins which were hitherto unknown.

Some examples of stereospecific enzymatic hydrolysis of N-acyl-L-aminoacid esters by subtilisin or chymotrypsin have already been disclosed in the literature. The cases described relate to the resolution of derivatives of aminoacids which occur naturally, chiefly in proteins. Resolution of these aminoacids was to a greater or lesser extent predictable on the basis of the known specificity of the proteolytic enzymes used (A. Berger, M. Smolarski, M. Kun and H. D. Bosshard, J. Org. Chem., 38 (1973) 457–460, German Offenlegungsschrift No. 2,804,892, U.S. Pat. No. 3,963,573, A. O. Barel and A. N. Glazer, J. Biol. Chem., 243 (1968), 1344–1348, K. Morihara and H. Tsuzuki, Arch. Biochem. Biophys., 129 (1969), 620–634 and T. N. Tattabiraman and W. B. Lawson, Biochem. J., 126 (1972), 645–657).

Resolution of the optical antipodes of the heterocyclic aminoacids of the formula (I) has not yet been described in the literature. According to Chemical Reviews 46 (1950), 69–153, in particular 119–122, the results obtained according to the invention were furthermore not to be expected.

Possible preferred proteolytic enzymes, are serine and sulfhydryl proteases, especially subtilisin (EC 3.4.4.16.), α-chymotrypsin (EC 3.4.4.5.), papain (EC 3.4.4.10), ficin or bromelain, the first two both having a serine radical in the active centre of the aminoacid chain, whilst the latter have cysteine as the active centre in the aminoacid chain. Subtilisin is particularly preferred.

Proteolytic enzymes which are isolated from Bacillus subtilis and Bacillus licheniformis and are added to detergents to remove protein residues are particularly suitable. These industrial enzymes are chiefly known by the Trade Marks "Maxatase" (manufacturer: Gist-Brocades N.V., Delft/Netherlands), "Optimase" (manufacturer: Miles-Kali Chemie, Hanover) and "Alcalase" (manufacturer: Novo Industries AS, Copenhagen/Denmark). The manufacture of commercially available subtilisin preparation is described in M. Ottensen and I. Svendsen, Methods in Enzymology, Vol. 19, pages 199–215 special 202–205.

The properties of the proteolytic enzymes, in particular their biochemical actions, are described in the following literature references: G. E. Perlmann and L. Lorand, Methods in Enzymology, 19 (1970) 199–215; P. Desnuelle, The Enzymes, 4 (1960) 93 and G. E. Perlmann and L. Lorand, Methods in Enzymology, 19 (1970) 226–244.

The proteolytic enzymes can be coupled to polymeric carriers by a covalent bond via a lysine radical which is not essential for catalysis. The carrier-bonded enzymes formed by convalent bonding of the enzyme to the carrier lose their activity only very slowly, after frequent re-use. Another possibility is adsorption of the enzyme onto the pores of a charged carrier and subsequent crosslinking with glutarodialdehyde.

Possible preferred enzyme carriers are polymeric, porous carriers, such as cellulose, for example DEAE-cellulose or CM-cellulose, modified polyacrylamide gels with amino groups or hydroxyl groups, or organic copolymers of acrylamide, methacrylates or methacrylamide and maleic anhydride, according to U.S. Pat. Nos. 3,871,964 and 3,910,825.

For coupling to the polymeric carrier, the enzyme is reacted under conditions which are optimum for the stability of the enzyme. The effectiveness of the coupling can be determined by measuring the enzymatic activity in the polymer and in the wash water. When the batch process is used, the polymeric enzyme can easily be separated off from the reaction solution by sedimentation or filtration and can be employed several times. It is is also possible for the enzyme carrier to be filled into columns and for the substrate solution to flow through the columns in the presence of a buffer system.

A prior test for the adsorption of the starting products and end products is a pre-requisite for the suitability of an enzyme carrier for the process according to the invention. Suitable carriers should adsorb the starting products and end products only to a very slight extent or not at all.

The various celluloses, cellulose derivatives, polyacrylamide gels containing amino groups or hydroxyl groups and anhydride resins modified by amino groups or hydroxyl groups have proved particularly suitable carriers for the proteolytic anzymes. In general, all the polymeric carriers which have amino groups or hydroxyl groups and do not adsorb the starting products and end products of the process according to the invention can be employed as the carrier. The polymeric carrier is activated, by methods which are known per se, with cyanuric chloride (British Patent Specification 1,302,706, N. L. Smith and H. M. Lehnhoff, Arch. Biochem., 61 (1974) 392–415 and T. H. Finlay et al., Arch. Biochem., 87 (1978) 77–90) or various halogenopyrimidines, according to British Pat. No. 1,527,975 or U.S. Pat. No. 4,144,128 issued Mar. 13, 1979.

The N-acyl esters and -amides, employed in the process according to the invention, of the heterocyclic aminoacids are obtained by acylating the corresponding aminoacid ester hydrochlorides or amide hydrochlorides with stoichiometric amounts of an acid anhydride, such as acetic anhydride, and then separating off the N-acyl derivative from the aqueous phase with organic solvents, such as chloroform or methylene chloride.

The enzymatic resolution is preferably carried out at a temperature of 20°–40° C. in a pH range of 6 to 8, the pH value preferably being kept constant at 7.0 by adding a strong base. The substrate is generally added as an approximately 10–20% strength organic solution to a suspension of the carrier-bonded enzyme in water, it being possible for the proportion of solvent, relative to the total volume, to be at most 75–80% by volume. The reaction medium is stirred intensively throughout the enzymatic reaction. The progress and the end point of the enzymatic reaction can be established by neutralisation of the $H^+$ ions formed. The neutralisation can be effected either by inorganic bases or by organic bases.

Preferred water-immiscible solvents for the process according to the invention are methylene chloride, chloroform, toluene, benzene, ethyl acetate, petroleum ether, methyl isobutyl ketone or isobutanol.

Numerous substrates and products of enzyme reactions are soluble only to a limited extent in water or buffer solutions. However, for economic reasons, substrate solutions which are as concentrated as possible should be employed when reactions with carrier-bonded enzymes are carried out industrially.

Numerous attempts have thus been made to achieve higher product concentrations with enzymes in water/solvent mixtures than in aqueous solution.

The results show that dissolved, solvated enzymes can be partly or completely denatured, with partial or complete loss of enzyme activity, and can be precipitated from the solution by solvents such as methanol, ethanol, acetone, acetonitrile, dioxane and dimethylformamide or dimethylsulphoxide.

Bonding the enzyme to a polymeric carrier prevents aggregation of the enzyme molecules, so that carrier-bonded enzymes lose their activity to a considerably lesser extent than the free enzymes (K. Tamizawa and M. L. Bender, J. Biol. Chem. 249 (1974), 2130–2134). However, a greater or lesser loss of activity of the bonded enzyme through the solvent is also observed with carrier-bonded enzymes. Either an irreversible or a reversible inactivation of the enzyme, as a function of the concentration of the solvent, is observed (H. Kaplan and K. J. Leidler, Canad. J. Chem. 45 (1967), 547–557, G. M. Umezurike, Biochem. J. 167 (1977), 831–833, T. N. Pattabiraman and W. B. Lawson, Biochem. J. 126 (1972), 645–657, G. Fink and H. Thoma. DECHEMA Monograph 71, 295–314 and H. Wan and C. Horvath, Biophys. Biochem. Acta 410 (1973), 135–140).

The enzyme activity can also be altered by a change in the pore size of the enzyme carrier, as a result of the influence of the solvent.

However, the abovementioned completely water-miscible solvents have the further industrial disadvantage that they are difficult to separate off from water by distillation.

The use of water-immiscible solvents in reactions with carrier-bonded enzymes has hitherto been described in only one case in the literature (A. M. Klibanov, G. P. Samokhin, K. Martinek and I. V. Berezin, Biotechnol, Bioeng. 19 (1977) 1351–1361). The work quoted describes the synthesis of N-acetyl-L-tryptophan ethyl ester from N-acetyl-L-tryptophan and ethanol with chymotrypsin covalently bonded to glass, in chloroform as the solvent. In order to be able to carry out the synthesis of the ester, which is unfavourable for energetic reasons, the reaction must be carried out in the absence of water. This literature reference thus gives no indication at all of the process according to the invention.

The process according to the invention avoids all the disadvantages mentioned, and furthermore protects the N-acyl-aminoacid ester from non-specific hydrolysis, so that the enzymatic resolution can also be carried out at higher pH values without loss of yield.

After covalent bonding to a polymeric carrier, the carrier-bonded enzyme can be protected from the denaturing action of solvents by subsequent inter- and intramolecular crosslinking with bivalent or polyvalent reagents, such as glutarodialdehyde or other reagents (F. Wold, Methods in Enzymology XI, 617–640).

When the enzymatic reaction has ended and after the enzyme resin has settled, the organic phase is separated off and the aqueous reaction solution is extracted in portions again with twice the volume of the organic solvent. The extracts are combined. The enzyme resin is filtered off and the aqueous phase which remains is rendered acid, for example with a mineral acid, such as sulphuric acid, and extracted with ethyl acetate. The optical purity of the resulting compounds is then investigated.

To prepare the heterocyclic D- or L-aminoacids, the protective groups $R_2$ and $R_4$ are split off in a manner customary to the expert. For example, D-α-furylglycine is obtained from D-α-formamidofurylacetic acid methyl ester by warming with dilute hydrochloric acid.

Examples 1 to 4 illustrate the preparation of carriers having proteolytic enzymes bonded thereto and Examples 5 and 6 illustrate the preparation of compounds of the present invention.

EXAMPLE 1

200 g of Cellulose Avicel (Merck) are suspended in a solution of 500 ml of water and 500 ml of dioxane, and 20 g of cyanuric chloride are added. The pH value is kept between 7.0 and 9.0 with 2 N NaOH. After stirring for 45 minutes, the activated cellulose was filtered off over a frit and suspended in 800 ml of water. 25 g of Maxatase (Gist-Brocades N.V., Delft/Netherlands) are added and the mixture is stirred at room temperature and at pH 7 to 8 for 20 hours. Thereafter, the supported enzyme is filtered off over a frit, washed in portions with distilled water and finally sucked dry.

600 g of moist subtilisin-cellulose are obtained. Activity: 284 ATEE (N-acetyl-L-tyrosine ethyl ester) units/g of supported enzyme. Total activity: 170,250 ATEE units, corresponding to 27.2% of the activity employed.

ATEE-units are defined in R. Ruyssen and A. Lauwers, Pharmaceutical Enzymes, Scientific Publishing Company, Gent/Belgium, 1978, pages 41–55.

EXAMPLE 2

100 g of DEAE-cellulose (DE-52-Cellulose, Messrs. Whatmann, Springfield/England) are activated with cyanuric chloride in a manner similar to that described above. 5 g of Maxatase or Alcalase, lyophilised after dialysis against water (659 Anson units/g, manufacturer: Novo AS, Copenhagen/Denmark) are covalently bonded thereto. After filtration, 140 g of moist DE-52-Cellulose-subtilisin with 740 ATEE units/g of supported enzyme are obtained.

The total yield of activity is 103,600 ATEE units, corresponding to 16.5% of the activity employed.

EXAMPLE 3

20 g of anhydride resin (80% by weight of tetraethylene glycol dimethacrylate, 10% by weight of methacelylic acid and 10% by weight of maleic anhydride) washed with acetone are suspended in 50 ml of water. 40 ml of 10% strength by weight hexamethylenediamine solution or ethanolamine solution are added at pH 7.0 and the suspension is kept at a constant pH of 6.2 overnight by titration. The amine resin is filtered off. Excess hexamethylenediamine is washed out with 1 M NaCl solution. The resin is then washed with desalinated water.

The anhydride resin carrying amino groups is suspended in 50 ml of water and 50 ml of dioxane and is activated with 2 g of cynauric chloride at room temperature and at pH 5.0 for 1 hour. The resin is washed with dioxane and water and reacted with 2 g of Maxatase at room temperature and at pH 8.0 for 20 hours.

48.2 g of moist resin with an activity of 126 ATEE units/g of carrier-bonded enzyme are obtained.

The total yield of activity is 60,790 ATEE units, corresponding to 12.1% of the activity employed.

EXAMPLE 4

300 g of polyacrylonitrile resin, which has been reacted with diethylenetriamine, is activated in a weight ratio of carrier:cyanuric chloride of 10:1 and reacted with 30 g of Maxatase at 25° C. and at pH 8.0 for 16 hours, as indicated above.

288.5 g of moist enzyme resin are obtained.

The proteolytic activity on the carrier is 81.0 ATEE units/g of enzyme resin. The total activity is 23,383 ATEE units, corresponding to 3.1% of the total activity employed.

EXAMPLE 5

(5.1) Preparation of D,L-α-formamidofurylacetic acid methyl ester

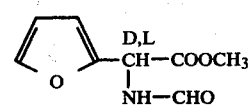

390 ml of formic acid are added dropwise to 810 ml of acetic anhydride at 35° C. The mixture is then stirred at 55° C. for one hour. 14.1 g of D,L-α-furylglycine are introduced in portions into 100 ml of the above mixed anhydride, during which the temperature is not allowed to exceed 30° C. About 6 minutes after the last addition, the formylated aminoacid starts to separate out. After stirring the mixture for 3 hours, the product is filtered off, washed twice with diethyl ether and dried in air. 13.2 g (78% of theory) of beige crystals of melting point 170°–172° C. (decomposition) are employed.

13.0 g of the compound obtained above are dissolved in 40 ml of dimethylsulphoxide, and a solution of 3.08 g of sodium hydroxide in 17 ml of water is added in portions, whilst cooling with ice. 32.7 g of methyl iodide are then added, whereupon two phases are formed. After stirring the reaction mixture at room temperature for 50 hours, it is poured into 150 ml of water and extracted five times by shaking with 200 ml of methylene chloride each time. The combined organic phases are then shaken twice with 50 ml of 2% strength sodium sulphite solution each time and dried over sodium sulphate. After concentration, 10.6 g (75.3% of theory) of product are obtained as an oil, which crystallizes when seeded; melting point: 52°–55° C.

(5.2) Preparation of D-α-Formamidofurylacetic acid methyl ester 30.0 g of the product obtained according to Example 5 (a) are dissolved in 800 ml of distilled water and resolved with 132.5 g of cellulose-subtilisin ($10^5$ ATEE units) at pH 6.5 and at 25° C. The pH value is kept constant at 6.5 with 25% strength $NH_3$. After 2.5 hours, the carrier-bonded enzyme is filtered off and washed twice with 100 ml of water. The desired compound is extracted from the filtrate with four 100 ml portions of methylene chloride. The yield was 11.2 g (74% of theory).

$[\alpha]_{578\,nm}^{25°\,C.} = -179.8°$, c=1 in methanol.

The aqueous phase is adjusted to pH 1.5 with sulphuric acid and extracted four times with 100 ml of ethyl acetate each time. The combined ethyl acetate extracts are evaporated to dryness in vacuo. The yield of L-α-formamidofurylacetic acid is 11 g (79% of theory).

$[\alpha]_{578\,nm}^{25°\,C.} = +162.7°$, c=1 in methanol.

(5.3) Preparation of D-α-furylglycine hydrochloride 44.0 g of the product obtained according to Example 5(b) are dissolved in 440 ml of 2 N hydrochloric acid under the influence of heat and the solution is kept at 80° C. for 70 minutes, decolorised with animal charcoal and concentrated.

The residue is digested with a mixture of 80 parts of acetone and 40 parts of ethanol and is filtered off. The product is washed with acetone and dried in vacuo. 26.0 g (61% of theory) of D-α-furylglycine hydrochloride with a melting point of 193°–195° C. (decomposition) are obtained.

$[\alpha]_{578\,nm}^{25°\,C.} = -114.9°$ c=1 in methanol.

L-α-Furylglycine hydrochloride is obtained from L-α-formamido furylacetic acid (5.2.) by dissolving in 2 N hydrochloric acid and warming the solution to 80° C. for 70 minutes. It is isolated in the same manner as described for D-α-furylglycine.

EXAMPLE 6

(6.1) Preparation of D,L-α-t-butoxycarbonylaminofurylacetic acid

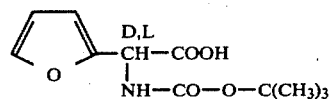

5.0 g of D,L,-α-furylglycine in 100 ml of 80% strength aqueous dioxane are brought to pH 8 with 4 N sodium hydroxide solution. 8.0 g of 2-(t-butoxycarbonyloximino)-2-phenylacetonitrile are added and the mixture is warmed to 70° C. for 2 hours. During this period, the above pH value is maintained by adding 4 N sodium hydroxide solution. 80 ml of water are then added, the dioxane is distilled off and the mixture is extracted several times with ethyl acetate. The aqueous phase is brought to pH 4 with 10% strength citric acid, saturated with sodium chloride and extracted by shaking with ethyl acetate. The ethyl acetate phases are dried over sodium sulphate and concentrated. The residue is crystallised from a little absolute carbon tetrachloride. 4.3 g of D,L-α-t-butoxycarbonylaminofurylacetic acid of melting point 99°–101° C. are obtained.

(6.2) Preparation of D,L-α-t-butoxycarbonylaminofurylacetic acid methyl ester

Ethereal diazomethane solution is added dropwise to a solution of 6.0 g of the compound obtained according to Example 6(a) in 100 ml of absolute diethyl ether until the yellow coloration remains. The mixture is then extracted by shaking with dilute sodium hydroxide solution and the product phase is washed with water, dried over sodium sulphate and evaporated. 6.1 g (96% of theory) of the desired compound of melting point 63°–68° C. are obtained.

(6.3) Enzymatic resolution of D,L-α-t-butoxycarbonylaminofurylacetic acid methyl ester in the presence of methyl isobutyl ketone 20 g of the compound obtained according to Example 6(b) are dissolved in a mixture of 800 ml of water and 200 ml of methyl isobutyl ketone and are resolved with the subtilisin-carrier resin prepared according to Example 4, at pH 7.0 and 37° C., whilst stirring. The pH value is kept constant with 25% strength ammonia. After a reaction time of 5 hours, the stirrer is switched off and the organic phase is separated off from the aqueous phase. The aqueous phase is then extracted twice more with 200 ml of methyl isobutyl ketone each time. The combined organic phases are evaporated to dryness in vacuo. The yield of D-α-t-butoxycarbonylaminofurylacetic acid methyl ester is 10.2 g (68% of theory).

$[\alpha]_{578\,nm}^{25°\,C.} = -81.4°$, c=1 in methanol.

The aqueous phase which remains is adjusted to pH 1.5 with sulphuric acid and extracted with four 100 ml portions of ethyl acetate.

The yield of L-α-t-butoxycarbonylaminofurylacetic acid is 8.8 g (93% of theory).

$[\alpha]_{578\,nm}^{25°\,C.} = +104.7°$, c=1 in methanol.

(6.4) Preparation of D-α-Furylglycine hydrochloride 10.0 g of D-α-t-butoxycarbonylaminofurylacetic acid methyl ester are dissolved in a mixture of 100 ml of 2 N hydrochloric acid and 45 ml of dioxane under the influence of heat and the solution is kept at 80° C. for 2 hours, treated with active charcoal and evaporated. The residue is digested with a mixture of 20 ml of acetone and 10 ml of ethanol, filtered off, washed with acetone and dried. 3.9 g of D-α-furylglycine hydrochloride are obtained.

[α]$_{578\,nm}^{25°\,C.}$ = −109.2°, c=1 in methanol.

EXAMPLE 7.1

D,L-α-Formamido-(5-methyl-isoxazol-3-yl)-acetic acid methyl ester

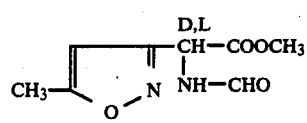

is prepared analogously to Example 5.1.

EXAMPLE 7.2

D-α-Formamido-(5-methyl-isoxazol-3-yl)-acetic acid methyl ester is prepared analogously to Example 5.2.

EXAMPLE 7.3

D-α-(5-Methyl-isoxazol-3-yl)-glycin-hydrochloride

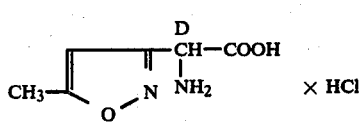

is prepared analogously to Example 5.3.

EXAMPLE 8.1

D,L-α-Formamido-pryid-3-yl-acetic acid methyl ester

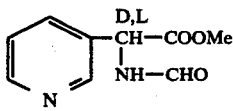

is prepared analogously to Example 5.1

EXAMPLE 8.2

D-α-Formamido-pyrid-3-yl-acetic acid methyl ester is prepared analogously to Example 5.2.

EXAMPLE 8.3

D-α-Pyrid-3-yl-glycin-dihydrochloride

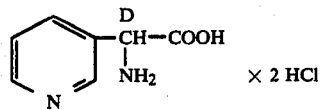

is prepared analogously to Example 5.3

EXAMPLE 9.1

D,L-α-Formamido-thiazol-2-yl-acetic acid methyl ester

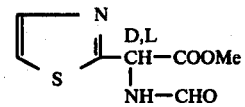

is prepared according to the method of Example 5.1.

EXAMPLE 9.2

D-α-Formamido-thiazol-2-yl-acetic acid methyl ester is prepared according to the method of Example 5.2.

EXAMPLE 9.3

D-α-Thiazol-2-yl-glycin-hydrochloride

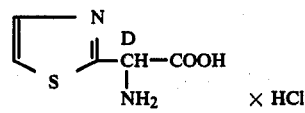

is prepared according to the method of Example 5.3.

EXAMPLE 10.1

D,L-α-Formamido-indol-3-yl-acetic acid methyl ester

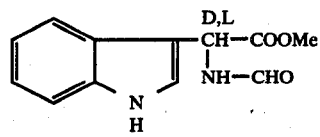

is prepared as in Example 5.1.

EXAMPLE 10.2

D-α-Formamido-indol-3-yl-acetic acid methyl ester is prepared as in Example 5.2.

EXAMPLE 10.3

D-α-Indol-3-yl-glycin-hydrochloride

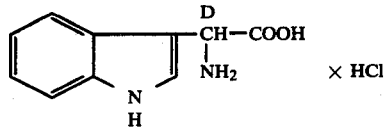

is prepared as in Example 5.3.

EXAMPLE 11.1

D,L-α-Formamido-(5-chlorofuryl)-acetic acid methyl ester

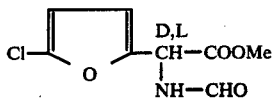

is prepared as in Example 5.1.

EXAMPLE 11.2

D-α-Formamido-(5-chlorofuryl)-acetic acid methyl ester is prepared as in Example 5.2.

EXAMPLE 11.3

D-α-5-Chlorofuryl-glycin-hydrochloride

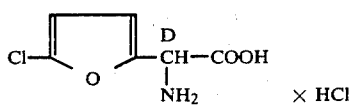

is prepared as in Example 5.3.

What is claimed is:

1. A process for the production of a compound which is an optically pure heterocyclic aminoacid of the general formula

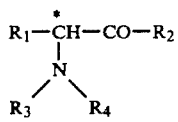 (I)

or a salt, preferably a pharmaceutically acceptable salt, thereof, in which $R_1$ denotes a saturated or unsaturated, optionally substituted heterocyclic radical which contains 1 to 4 identical or different heteroatoms selected from oxygen, sulphur and nitrogen and is optionally benzo-fused, $R_2$ denotes a hydroxyl group, a $C_1$ to $C_4$ alkoxy group or a $N(R_5)_2$ radical, $R_3$ and $R_4$ independently denote a hydrogen atom, an acyl radical or a $C_2$ to $C_4$ alkenyl radical which is substituted by $C_1$ to $C_4$ alkoxy carbonyl and $R_5$ denotes a hydrogen atom or a $C_1$ to $C_4$ alkyl group, and in which the carbon atom marked with * is in either the D-form or the L-form which comprises subjecting a racemic compound of the formula (I) in which $R_1$, $R_3$ and $R_5$ are defined as above, $R_2$ denotes a $C_1$ to $C_4$ alkoxy group or a $N(R_5)_2$ radical and $R_4$ denotes an acyl radical, or a $C_2$ to $C_4$ alkenyl radical which is substituted by $C_1$ to $C_4$ alkoxycarbonyl, to a proteolytic enzyme bonded to a carrier in a two-phase medium consisting of water and and water-immiscible solvent, separating off the unchanged D-compound from the L-compound of the formula

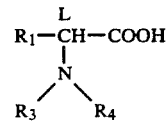

in which $R_1$, $R_3$ and $R_4$ have the above-mentioned meaning, and, if desired, converting the D- and L-compounds which have been separated from each other into compounds of the formula (I) in which $R_2$ denotes a hydroxyl group and $R_3$ and $R_4$ denote hydrogen atoms, and in the case of the L-compound converting, if desired, the carboxyl group into a $-COR_2$ group in which $R_2$ denotes $C_1$ to $C_4$ alkoxy group or a $N(R_5)_2$ radical in which $R_5$ has the above-mentioned meaning.

2. A process according to claim 1, in which the proteolytic enzyme is subtilisin, α-chymotrypsin, papain, ficin or bromelain.

3. A process according to claim 1, in which the water-immiscible solvent is methylene chloride, chloroform, toluene, benzene, ethyl acetate, petroleum ether, methyl isobutyl ketone or isobutanol.

4. A process according to any of claims 1, 2 or 3 in which the carrier for the proteolytic enzyme is a cellulose, a cellulose derivative, a polyacrylamide gel containing amino groups or hydroxyl groups or an anhydride resin modified by amino groups or hydroxyl groups.

* * * * *